(12) United States Patent
Andrews et al.

(10) Patent No.: US 7,790,926 B2
(45) Date of Patent: Sep. 7, 2010

(54) ALPHA, OMEGA-DIFUNCTIONAL ALDARAMIDES

(75) Inventors: Mark Allen Andrews, Wilmington, DE (US); Henry Keith Chenault, Hockessin, DE (US); Garret D. Figuly, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 210 days.

(21) Appl. No.: 12/023,649

(22) Filed: Jan. 31, 2008

(65) Prior Publication Data

US 2008/0177050 A1 Jul. 24, 2008

Related U.S. Application Data

(62) Division of application No. 11/360,309, filed on Feb. 23, 2006, now Pat. No. 7,351,862.

(60) Provisional application No. 60/655,647, filed on Feb. 23, 2005.

(51) Int. Cl.
C07C 231/02 (2006.01)
C07C 233/05 (2006.01)

(52) U.S. Cl. .............. 564/158; 564/152; 564/160; 562/433; 562/553; 560/19; 560/155

(58) Field of Classification Search ............... 560/19, 560/155; 562/433, 553; 564/152, 158, 160
See application file for complete search history.

(56) References Cited

U.S. PATENT DOCUMENTS

| 4,833,230 | A | 5/1989 | Kiely et al. |
| 5,434,233 | A | 7/1995 | Kiely et al. |
| 7,351,862 | B2 * | 4/2008 | Andrews et al. ............ 564/158 |
| 2003/0158152 | A1 | 8/2003 | Pecanha et al. |
| 2005/0261418 | A1 | 11/2005 | Andrews et al. |
| 2005/0261430 | A1 | 11/2005 | Bouhelal |

FOREIGN PATENT DOCUMENTS

WO 2005/082978 A1 9/2005

OTHER PUBLICATIONS

Gorman et al, J. Biological Chemistry, 1980, pp. 1175-1180.*
Pecanha et al, Farmaco, 58, 149-157, 2003.*
Bonnet et al., Synthesis of an Amphiphilic Aldehyde Using As a Key Step the Condensation of a Lipophilic Glyoxylic Acid Amide Derivative With TRIS (Hydroxymethyl) Aminomethane, Tetrahedron Letters, 2001, vol. 42, pp. 1875-1877.
Ghosh et al., Toward Chiral Polyamidoamine (PAMAM) Dendritic Architecture With Tartaric Acid Core, J. Indian Chem. Soc., 2002, vol. 79, pp. 442-443.
Donald E. Kiely et al., Hydroxylated Nylons Based on Unprotected Esterified D-Glucaric Acid by Simple Condensation Reactions, J. Am. Chem. Soc., 1994, vol. 116, pp. 571-578.
International Search Report Dated Oct. 31, 2006; International Appln. No. PCT/US06/006758.

* cited by examiner

*Primary Examiner*—Shailendra Kumar

(57) ABSTRACT

Alpha, omega-difunctional aldaramides, in particular diaminoaldaramides, dihydroxyaldaramides, bis(alkoxycarbonylalkyl)aldaramides, and bis(carboxyalkyl)aldaramides, and processes for preparing the aldaramides are provided.

16 Claims, No Drawings

ALPHA, OMEGA-DIFUNCTIONAL ALDARAMIDES

RELATED APPLICATION

This application is a Divisional of co-owned application no. 11/360,309, filed on Feb. 23, 2006, now U.S. Pat. No. 7,351,862, which claims benefit of 60/655,647, filed Feb. 23, 2005.

FIELD OF INVENTION

The invention is directed to alpha, omega-difunctional aldaramides and processes for preparing them.

BACKGROUND

The concept of using biomass-derived materials to produce other useful products has been explored since man first used plant materials and animal fur to make clothing and tools. Biomass derived materials have also been used for centuries as adhesives, solvents, lighting materials, fuels, inks/paints/coatings, colorants, perfumes and medicines. Recently, people have begun to explore the possibility of using "refined biomass" as starting materials for chemical conversions leading to novel high value-in-use products. Over the past two decades, the cost of renewable biomass materials has decreased to a point where many are competitive with those derived from petroleum. In addition, many materials that cannot be produced simply from petroleum feedstocks are potentially available from biomass or refined biomass. Many of these unique, highly functionalized, molecules would be expected to yield products unlike any produced by current chemical processes. "Refined biomass" is purified chemical compounds derived from the first or second round of plant biomass processing. Examples of such materials include cellulose, sucrose, glucose, fructose, sorbitol, erythritol, and various vegetable oils.

A particularly useful class of refined biomass is that of aldaric acids. Aldaric acids, also known as saccharic acids, are diacids derived from naturally occurring sugars. When aldoses are exposed to strong oxidizing agents, such as nitric acid, both the aldehydic carbon atom and the carbon bearing the primary hydroxyl group are oxidized to carboxyl groups. An attractive feature of these aldaric acids includes the use of very inexpensive sugar based feedstocks, which provide low raw material costs and ultimately could provide low polymer costs if the proper oxidation processes are found. Also, the high functional density, of these aldaric acids, provides unique, high value opportunities, which are completely unattainable at a reasonable cost from petroleum-based feedstocks.

Aldaric acid derivatives, because of their high functionality, are potentially valuable monomers and crosslinking agents.

Diaminoaldaramides, dihydroxyaldaramides, bis(alkoxycarbonylalkyl)aldaramides, and bis(carboxyalkyl)aldaramides are examples of monomers and crosslinking agents that could be prepared. No simple method exists for the preparation of all of these. Hoagland (Carbohydrate Res., 98 (1981) 203-208) studied the kinetics of the aminolysis of diethyl galactarate. This procedure would not be expected to produce the same results using the equivalent lactone or dilactone. Reaction of a polyhydroxy diester or dilactone with a diamine has the potential to produce oligomers and polymer and to undergo various side reactions. Gorman and Folk (J. Biol. Chem. 1980, 255, 1175-1180) employ a 4-step sequence to protect one end of ethylenediamine, react with diethyl tartrate, and deprotect. It would be expected that an aminoester would not react with another ester without competing reaction with itself to form oligopeptides. Pecanha, et al. (WO02/42412) employ a four-step sequence to protect the hydroxyl groups of tartaric acid, activate the carboxyl groups as acyl chloride groups, react with an amino acid ester, and deprotect.

Applicants have discovered new difunctional aldaramides that can be used as monomers or polymer crosslinkers, and processes for preparing the aldaramides.

SUMMARY OF THE INVENTION

One aspect of the invention is a compound of Formula I

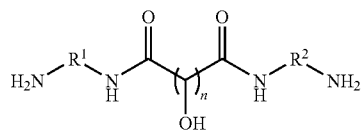

and salts thereof, wherein n=1-6 and $R^1$ and $R^2$ are independently optionally substituted hydrocarbylene groups, wherein the hydrocarbylene groups are aliphatic or aromatic, linear, branched, or cyclic, and wherein the hydrocarbylene groups optionally contain —O— linkages.

Another aspect of the invention is a compound of Formula V,

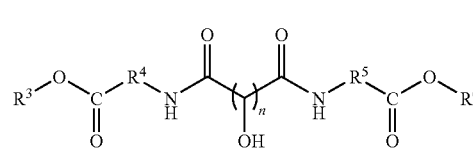

and salts thereof, wherein n=1-6; $R^4$ and $R^5$ are independently optionally substituted hydrocarbylene groups, wherein the hydrocarbylene groups are aliphatic or aromatic, linear, branched, or cyclic, and wherein the hydrocarbylene groups optionally contain —O— linkages; and $R^3$ and $R^6$ are independently hydrogen, optionally substituted aryl or optionally substituted alkyl.

Another aspect of the invention is a process for preparing a compound of Formula VII

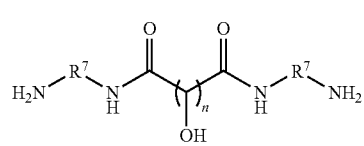

or a salt thereof, comprising contacting at least one diamine of the formula $NH_2$—$R^7$—$NH_2$ with a compound of Formula VIII, IX, or X wherein $R^7$ is an optionally substituted hydrocarbylene group, wherein the hydrocarbylene group is aliphatic or aromatic, linear, branched, or cyclic, and wherein the hydrocarbylene group optionally contains —O— linkages, R' and R" are independently a 1 to 6 carbon alkyl group, n=1-6, m=0-4, and p=1-4.

Another aspect of the invention is a process for preparing a compound of Formula XIX

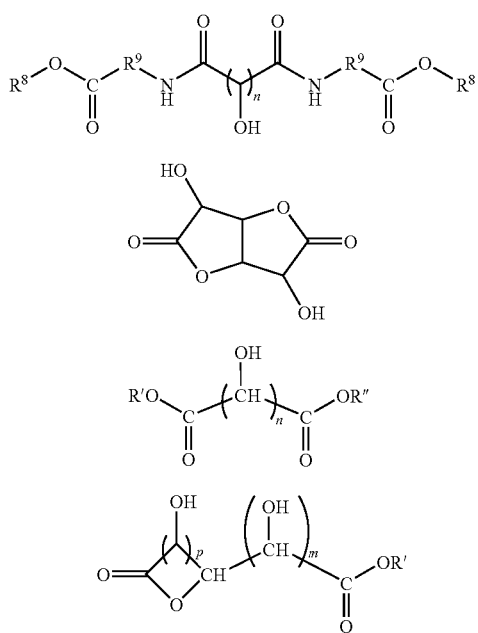

or a salt thereof, comprising contacting at least one amino acid or amino acid ester of the formula $(R^8OOC)$—$R^9$—$NH_2$ with a compound of Formula VIII, IX, or X, wherein n=1-6; $R^9$ is an optionally substituted hydrocarbylene group, wherein the hydrocarbyl group is aliphatic or aromatic, linear, branched, or cyclic, and wherein the hydrocarbylene group optionally contains —O— linkages, $R^8$ is hydrogen or alkyl, R' and R" are independently a 1 to 6 carbon alkyl group, n=1-6, m=0-4, and p=1-4.

Another aspect of the invention is a process for preparing a compound of the Formula XXII

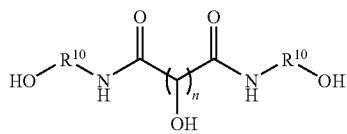

or salts thereof, comprising contacting at least one aminoalcohol of the Formula HO—$R^{10}$—$NH_2$ with a compound of Formula VIII or X wherein $R^{10}$ is an optionally substituted hydrocarbylene group, wherein the hydrocarbylene group is aliphatic or aromatic, linear, branched, or cyclic, and wherein the hydrocarbylene group optionally contains —O— linkages, R' is a 1 to 6 carbon alkyl group, m=0-4, and p=1-4.

DETAILED DESCRIPTION

The following definitions can be used for the interpretation of the specification and the claims:

By hydrocarbyl is meant a straight chain, branched or cyclic arrangement of carbon atoms connected by single, double, or triple carbon-to-carbon bonds, and substituted accordingly with hydrogen atoms. Hydrocarbyl groups can be aliphatic and/or aromatic. Examples of hydrocarbyl groups include methyl, ethyl, propyl, isopropyl, butyl, isobutyl, t-butyl, cyclopropyl, cyclobutyl, cyclopentyl, methylcyclopentyl, cyclohexyl, methylcyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl. Examples of substituted hydrocarbyl groups include tolyl, chlorobenzyl, —$(CH_2)$—O—$(CH_2)$—, fluoroethyl, p-$(CH_3S)C_6H_5$, 2-methoxypropyl, and $(CH_3)_3SiCH_2$.

"Alkyl" means a saturated hydrocarbyl group. Examples of alkyl groups include methyl, ethyl, propyl, isopropyl, butyl, s-butyl, isobutyl, pentyl, neopentyl, hexyl, heptyl, isoheptyl, 2-ethylhexyl, cyclohexyl and octyl.

"Aryl" means a group defined as a monovalent radical formed conceptually by removal of a hydrogen atom from a hydrocarbon that is structurally composed entirely of one or more benzene rings. Examples of aryl groups include benzene, biphenyl, terphenyl, naphthalene, phenyl naphthalene, and naphthylbenzene.

'Alkylene' and 'arylene' refer to the divalent forms of the corresponding alkyl and aryl groups. 'Hydrocarbylene' groups include 'alkylene' groups, 'arylene' groups, and groups that can be represented by connecting some combination of alkylene and arylene groups. "Divalent", as used herein, means that the group can form two bonds.

"Substituted" and "substituent" mean a group is substituted and contains one or more substituent groups, or "substituents," that do not cause the compound to be unstable or unsuitable for the use or reaction intended. Unless otherwise specified herein, when a group is stated to be "substituted" or "optionally substituted", substituent groups that can be present include amide, nitrile, ether, ester, halo, amino (including primary, secondary and tertiary amino), hydroxy, oxo, vinylidene or substituted vinylidene, silyl or substituted silyl, nitro, nitroso, and thioether.

The present invention is directed to difunctional aldaramides, including those that are useful as monomers or crosslinking agents for polymers. Co-pending patent applications Ser. Nos. 11/064,191 and 11/064,192 describe the use of some such materials in the preparation of cross-linked polymers.

Aldaric acids are diacids derived from naturally occurring sugars. When aldoses are exposed to strong oxidizing agents, such as nitric acid, both the aldehydic carbon atom and the carbon bearing the primary hydroxyl group are oxidized to carboxyl groups. This family of diacids is known as aldaric acids (or saccharic acids). An aldolactone has one carboxylic acid lactonized; the aldarodilactone has both lactonized. As illustration, the aldaric acid derivatives starting from D-glucose are shown below.

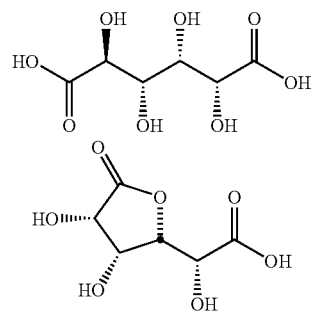

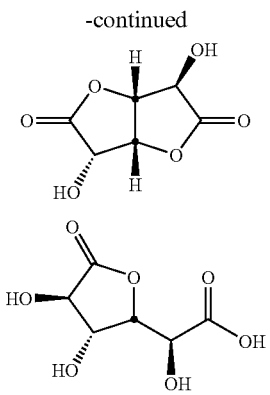

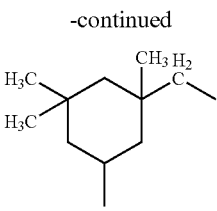

wherein the open valences indicate where $R^1$ and $R^2$ attach to the nitrogens in Formula I. In Formula IV, either open valence can be attached to the terminal, primary amino ($NH_2$) group.

In other embodiments, the present invention provides compounds of Formula V,

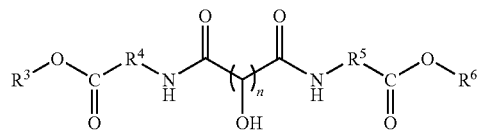

and salts thereof, wherein n=1-6; $R^4$ and $R^5$ are independently optionally substituted hydrocarbylene groups, wherein the hydrocarbylene groups are aliphatic or aromatic, linear, branched, or cyclic, and wherein the hydrocarbylene groups optionally contain —O— linkages; and $R^3$ and $R^6$ are independently hydrogen, optionally substituted aryl or optionally substituted alkyl.

$R^4$ and $R^5$ can be the same or different, and can independently be alkylene, polyoxaalkylene, or arylene groups, linear or branched, wherein the alkylene, polyoxaalkylene, or arylene groups are optionally substituted with $NH_2$ or alkyl. $R^4$ and $R^5$ can also be —$CH_2$—, —$CH_2(CH_3)$—, —$CH_2(CH_2)_2CH_2$—, —$CH(NH_2)(CH_2)_4$—, or —CH[NHC(=O)O-tert-butyl]$CH_2CH_2CH_2CH_2$—. The open valences in the above formulae indicate where $R^4$ and $R^5$ are attached to the nitrogen and carbonyl carbon in Formula V. Where $R^4$ and $R^5$ are unsymmetrical, both orientations are intended, unless the resulting chemical structure is unstable.

In some embodiments, $R^4$ and/or $R^5$ can be an alkylene, polyoxaalkylene, heteroarylene, or arylene group, linear or branched, wherein the alkylene, polyoxaalkylene, heteroarylene or arylene group is optionally substituted with $NH_2$, aryl including heteroaryl, or alkyl. In some embodiments, n is 4. When $R^4$ and/or $R^5$ is alkylene, it can have from 1 to 12 carbon atoms, preferably from 1 to 6. Also, "arylene" is intended to include arenedialkylene, e.g.:

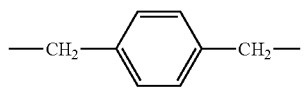

When $R^4$ and/or $R^5$ is arylene, it can have from 2 to 12 carbon atoms, preferably 4 to 6. For example, when $R^4$ and/or $R^5$ has two carbon atoms, it can be a heteroarylene, e.g., a triazole ring. When $R^4$ and/or $R^5$ has 12 carbon atoms, it can be, for example, a biphenyl. When $R^4$ and/or $R^5$ has 4 carbon atoms, examples are furan or pyrrole rings.

The compounds of the present invention and their starting materials can be made from aldaric acids or their derivatives, or from any other source. Any stereoisomer or mixture of stereoisomers can be used in the compositions and processes disclosed herein.

In some embodiments, the present invention provides compounds of Formula I and salts thereof, wherein n=1-6 and $R^1$ and $R^2$ are independently optionally substituted hydrocarbylene groups, wherein the hydrocarbylene groups are aliphatic or aromatic, linear, branched, or cyclic, and wherein the hydrocarbylene groups optionally contain —O— linkages. In some preferred embodiments, n=4.

$R^1$ and $R^2$ can be the same or different, and can independently be alkylene, polyoxaalkylene, or arylene groups, linear or branched, wherein the alkylene, polyoxaalkylene, or arylene groups are optionally substituted with $NH_2$ or alkyl. When $R^1$ or $R^2$ is alkylene, it can have from 2 to 20 carbon atoms, preferably from 2 to 8.

By "polyoxaalkylene" is meant linear or branched alkyl groups linked by ether linkages. Polyoxaalkylene can contain 2 carbons up to polymeric length units. Examples of polymeric polyoxaalkylenes suitable for the present inventions include poly(ethylene glycols), poly(propylene glycols), polyoxetane, and poly(tetramethylene glycols) such as those based on Terathane® polytetramethylene ether glycol (E. I. DuPont de Nemours, Wilmington, Del.).

$R^1$ and $R^2$ can also be independently —$CH_2$—$CH_2$—, —$CH_2(CH_2)_4CH_2$—, Formula II, Formula III, or Formula IV,

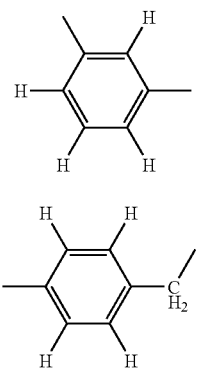

When $R^4$ and/or $R^5$ is polyoxaalkylene, it can have from 1 to 50 repeat units, preferably from 1 to 10. The total number of carbons depends on the number of carbons in the repeat unit.

In some embodiments, n=4. $R^3$ and $R^6$ can be the same or different, and can independently be hydrogen or methyl.

Also provided are processes for preparing difunctional aldaramides.

In some embodiments, the invention provides processes for preparing compounds of Formula VII

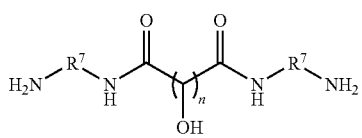

VII and salts thereof, comprising contacting at least one diamine of the formula $NH_2$—$R^7$—$NH_2$ with a compound of Formula VIII, IX, or X, shown below,

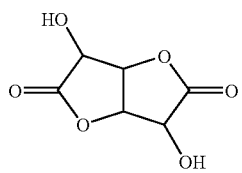

VIII

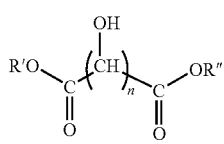

IX

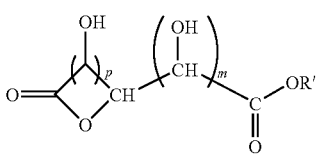

X wherein $R^7$ is an optionally substituted hydrocarbylene group, wherein the hydrocarbylene group is aliphatic or aromatic, linear, branched, or cyclic, and wherein the hydrocarbylene group optionally contains —O— linkages, R' and R" are independently a 1 to 6 carbon alkyl group, n=1-6, m=0-4, and p=1-4. In some embodiments of the invention, n=4.

$R^7$ can be an alkylene, polyoxaalkylene, or arylene group, linear or branched, wherein the alkylene, polyoxaalkylene, or arylene group is optionally substituted with $NH_2$ or alkyl. The diamine can also be $H_2NCH_2CH_2NH_2$, $H_2NCH_2(CH_2)_4CH_2NH_2$, Formula XI, Formula XII, or Formula XIII, shown below. With Formula XIII, either of the amino groups can react to form the amide bonds in Formula VII and, thus, either of the two amino groups of Formula XIII can remain as the residual primary amino ($NH_2$) groups in Formula VII.

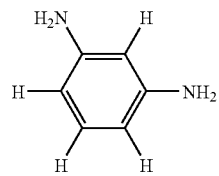

XI

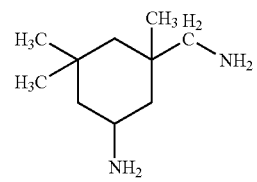

XII

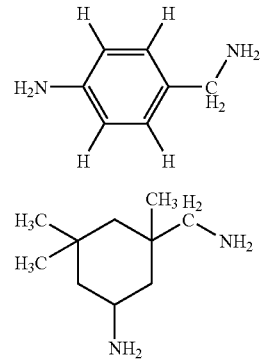

XIII

When $R^7$ is alkylene, it can have from 1 to 12 carbon atoms, preferably from 1 to 6. Also, "arylene" is intended to include arenedialkylene, e.g.:

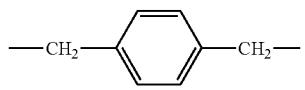

When $R^7$ is arylene, it can have from 2 to 12 carbon atoms, preferably 4 to 6. For example, when $R^7$ has two carbon atoms, it can be a heteroarylene, e.g., a triazole ring. When $R^7$ has 12 carbon atoms, it can be, for example, a biphenyl. When $R^7$ has 4 carbon atoms, examples are furan or pyrrole rings. When $R^7$ is polyoxaalkylene, it can have from 1 to 50 repeat units, preferably from 1 to 10. The total number of carbons depends on the number of carbons in the repeat unit.

In some embodiments, there are provided processes for preparing compounds of Formula XIX

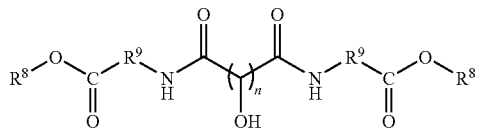

XIX and salts thereof, comprising contacting at least one amino acid or amino acid ester of the formula ($R^8OOC$)—$R^9$—$NH_2$ with a compound of Formula VIII, IX, or X, wherein n=1-6; $R^9$ is an optionally substituted hydrocarbylene group, wherein the hydrocarbylene group is aliphatic or aromatic, linear, branched, or cyclic, and wherein the hydrocarbylene group optionally contains —O— linkages, $R^8$ is hydrogen or alkyl, R' and R" are independently a 1 to 6 carbon alkyl group, n=1-6, m=0-4, and p=1-4.

In some embodiments, $R^9$ can be an alkylene, polyoxaalkylene, heteroarylene, or arylene group, linear or branched, wherein the alkylene, polyoxaalkylene, heteroarylene or arylene group is optionally substituted with $NH_2$, aryl including heteroaryl, or alkyl. In some embodiments, n is 4. When $R^9$ is alkylene, it can have from 1 to 12 carbon atoms, preferably from 1 to 6. Also, "arylene" is intended to include arenedialkylene, e.g.:

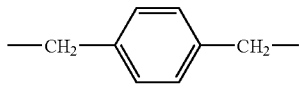

When $R^9$ is arylene, it can have from 2 to 12 carbon atoms, preferably 4 to 6. For example, when $R^9$ has two carbon atoms, it can be a heteroarylene, e.g., a triazole ring. When $R^9$ has 12 carbon atoms, it can be, for example, a biphenyl. When $R^9$ has 4 carbon atoms, examples are furan or pyrrole rings. When $R^9$ is polyoxaalkylene, it can have from 1 to 50 repeat units, preferably from 1 to 10. The total number of carbons depends on the number of carbons in the repeat unit.

The amino acid or amino acid ester can be $H_2NCH_2C(=O)OCH_3$, $H_2NCH(CH_3)C(=O)OCH_3$, $H_2N(CH_2)_4CH(NH_2)C(=O)OCH_3$, $H_2NCH(CH_3)C(=O)OH$, $H_2N(CH_2)_4CH(NH_2)C(=O)OH$, or Formula XX, shown below.

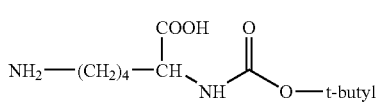

XX

Also provided is a process for preparing compounds of the Formula XXII

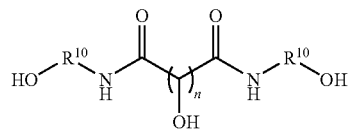

XXII and salts thereof, comprising contacting at least one aminoalcohol of formula $HO-R^{10}-NH_2$ with a compound of Formula VIII or X wherein $R^{10}$ is an optionally substituted hydrocarbylene group, wherein the hydrocarbylene group is aliphatic or aromatic, linear, branched, or cyclic, and wherein the hydrocarbylene group optionally contains —O— linkages.

$R^{10}$ can be an alkylene, polyoxaalkylene, or arylene group, linear or branched, wherein the alkylene, polyoxaalkylene, or arylene group is optionally substituted with $NH_2$ or alkyl. The aminoalcohol can be $HO-(CH_2)_2-NH_2$, $HO-(CH_2)_3-NH_2$, or 4-(2-aminoethyl)-phenol.

When $R^{10}$ is alkylene, it can have from 1 to 12 carbon atoms, preferably from 1 to 6. Also, "arylene" is intended to include arenedialkylene, e.g.:

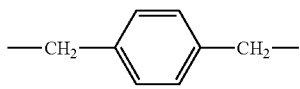

When $R^{10}$ is arylene, it can have from 2 to 12 carbon atoms, preferably 4 to 6. For example, when $R^{10}$ has two carbon atoms, it can be a heteroarylene, e.g., a triazole ring. When $R^{10}$ has 12 carbon atoms, it can be, for example, a biphenyl. When $R^{10}$ has 4 carbon atoms, examples are furan or pyrrole rings. When $R^{10}$ is polyoxaalkylene, it can have from 1 to 50 repeat units, preferably from 1 to 10. The total number of carbons depends on the number of carbons in the repeat unit.

The processes of the instant invention can be run at any suitable temperature but preferably at about 20° C. to about 130° C. The processes can also be prepared in the liquid phase or in the absence of any solvent. If prepared in the liquid phase, the reactants can be dissolved in a suitable solvent or mixture of solvents. The choice of solvent is not critical provided the solvent dissolves or disperses the reactants sufficiently to enable them to react within three days at a temperature of about 20° C. to about 130° C. and is not detrimental to reactant or product. Preferred solvents include water, dimethylformamide, dimethylformamide LiCl, dimethylacetamide, dimethylacetamide LiCl, ethanol, and methanol.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Diaminoaldaramides

Example 1

$N^1,N^6$-Bis(6-aminohexyl)galactaramide

To a 250-mL 3-neck round-bottom flask equipped with a heating mantle, reflux condenser, nitrogen inlet, and overhead stirrer were added 100 mL of a solution of LiCl (3.8 wt %) in dimethylacetamide (DMAC) and 10.0 g (0.042 mol) of dimethyl galactarate (DMG). The mixture was heated to 55° C. for about 80 minutes, after which a cloudy yellow mixture was obtained. To this stirred mixture was added 48.0 g (0.414 mol) of hexamethylenediamine (HMD). Within 5 minutes, the reaction temperature increased to 60° C., and a clear yellow solution was obtained. After an additional 5 minutes of stirring, a pale yellow precipitate formed. The reaction mixture was heated at 55° C. for an additional 5 hours. It was then left to cool overnight, after which the precipitate was collected by filtration, washed three times with THF, and dried in a vacuum oven at 60° C. to yield 26.4 g of crude product as white crystals. NMR revealed a large excess of HMD present. The crude product was recrystallized from ethanol and dried in a vacuum oven at 80° C. to yield 16.3 g (96%) purified product. $T_m$ (DSC): 178° C.; $T_{dec}$ (TGA): 160° C. (onset).

Example 2

$N^1,N^6$-Bis(2-aminoethyl)galactaramide

To a 250-mL 3-neck round-bottom flask equipped with a heating mantle, reflux condenser, nitrogen inlet, and overhead stirrer were added 100 mL of a solution of LiCl (3.8 wt %) in DMAC and 10.0 g (0.042 mol) of dimethyl galactarate (DMG). The mixture was heated to 55° C. for about 80 minutes. Ethylenediamine (26.0 g, 0.433 mol) was added. The mixture was heated at 55° C. for 5 hours and then cooled to room temperature. The resulting precipitate was collected by filtration, washed three times with THF, and dried in a vacuum oven at 60° C. to yield 18.60 g of crude product as white crystals. Recrystallization from ethanol and drying in a vacuum oven at 80° C. gave 10.93 g (89%) of purified product. $T_m$ (DSC): 217° C.; $T_{dec}$ (TGA): 190° C. (onset).

Example 3

$N^1,N^6$-Bis(6-aminohexyl)-D-glucaramide

To an oven-dried 20-mL scintillation vial equipped with a magnetic stir bar, in a dry box, were added D-glucaro-1,4:6,3-dilactone (GDL, 0.87 g, 4.98 mmol) dissolved in 3 mL of methanol followed by a solution of HMD (2.32 g, 19.9 mmol) in 5 mL of methanol. The mixture was stirred at ambient temperature for 18 hours. Additional methanol (10 mL) was added and the thick slurry was stirred at ambient temperature for an additional 5 days. The mixture was filtered and washed with methanol (30 mL) before vacuum drying to give an off-white solid (0.92 g, 45% yield). $^1$H NMR (300 MHz, DMSO-$d_6$) ϵ 7.81 (br, 1H), 7.57 (t, J=5.5 Hz, 1H), 3.97 (d, J=3.7 Hz, 1H), 3.92 (d, J=6.3 Hz, 1H), 3.86 (t, J=3.4 Hz, 1H), 3.68 (dd, J=3.0, 6.3 Hz, 1H), 3.41 (br, 8H), 3.07 (m, 4H), 2.51 (t, J=6.5 Hz, 4H), 1.41 (m, 4H), 1.26 (m, 12H). $^{13}$C NMR (75 MHz, DMSO-$d_6$) ϵ 173.23, 172.27, 73.40, 73.14, 71.79, 70.57, 41.64 (2C), 38.45, 38.36, 33.24 (2C), 29.32, 29.22, 26.42 (2C), 26.27 (2C).

Example 4

$N^1,N^6$-Bis(2-aminoethyl)-D-glucaramide

To a 250-mL 3-neck round-bottom flask equipped with a heating mantle, reflux condenser, nitrogen inlet, and overhead stirrer were added 50 mL of DMAC and 17.2 g (0.287 mol) of ethylenediamine. To the homogeneous solution formed was added, at room temperature, a solution of 5.0 g (0.0287 mol) of GDL dissolved in 25 mL of DMAC. At this point, heat was applied to the resulting homogeneous reaction mixture. When the temperature of the solution reached 38° C. after about 15 minutes of heating, a precipitate began to develop. The reaction temperature was increased to 50° C., and was held there for an additional 24 hours. The reaction mixture was cooled and then poured into about 100 mL of THF. The resulting precipitate was filtered, washed with THF, and dried in a vacuum oven at 80° C. to yield 6.92 g (82%) of a creamy white solid. $T_m$ (DSC): 181° C.; $T_{dec}$ (TGA): 170° C. (onset).

Example 5

$N^1,N^6$-Bis(2-aminoethyl)-D-glucaramide (Alternate Preparation)

To 48.9 g (814 mmol) of ethylenediamine dissolved in 400 mL of methanol were added dropwise, at room temperature, 22.18 g (127 mmol) of GDL dissolved in 100 mL of methanol. After stirring overnight at room temperature, the mixture was filtered. The precipitate was washed with methanol and dried under vacuum to give 33.1 g (89%) of a white solid that was an approximately 87:13 mixture of the 2:1 and 3:2 adducts of ethylenediamine and GDL. $^1$H NMR of $N^1,N^6$-bis(2-aminoethyl)-D-glucaramide (500 MHz, DMSO-$d_6$) ϵ 4.33 (d, J=3.1 Hz, 1H), 4.25 (d, J=5.2 Hz, 1H), 4.09 (dd, J=3.1, 4.7 Hz, 1H), 3.97 (t, J=5.0 Hz, 1H), 3.31 (m, 4H), 2.75 (m, 4H). $^{13}$C NMR of $N^1,N^6$-bis(2-aminoethyl)-D-glucaramide (126 MHz, DMSO-$d_6$) ϵ 175.30, 174.93, 73.62, 73.32, 73.04, 71.48, 41.95, 41.88, 40.41 (2C).

When the reaction was run similarly except using 10 mole equivalents of ethylenediamine relative to GDL, the ratio of 2:1 adduct to 3:2 adduct increased to about 95:5.

Example 6

$N^1,N^6$-Bis(3-aminophenyl)galactaramide

In a dry box, m-phenylenediamine (MPD, 0.92 g, 8.51 mmol) and DMG (0.51 g, 2.13 mmol) were weighed into an oven-dried 50-mL Schlenk tube. A metal spatula was used to grind the crystalline MPD and homogenize the reaction mixture. The mixture was heated under an atmosphere of nitrogen to 130° C. for 17 hours. $^1$H and $^{13}$C NMR (DMSO-$d_6$) indicated >95% conversion to the desired product with the remainder being methyl N-(3-aminophenyl)galactaramate. Heating the mixture to 130° C. for an additional three days increased conversion, but not to completion. Washing the reaction mixture with methylene chloride (85 mL) removed most of the excess MPD and halved the amount of methyl N-(3-aminophenyl)galactaramate. Subsequent recrystallization from DMAC/ether removed essentially all of the MPD and methyl N-(3-aminophenyl)galactaramate. $^1$H NMR (500 MHz, DMSO-$d_6$) ϵ 9.02 (s, 2H), 7.00 (s, 2H), 6.92 (t, J=7.9 Hz, 2H), 6.73 (d, J=8.0 Hz, 2H), 6.27 (d, J=8.0 Hz, 2H), 5.56 (d, J=7.1 Hz, 2H), 5.03 (br, 2H), 4.62 (m, 2H), 4.27 (d, J=7.0 Hz, 2H), 3.88 (m, 2H). $^{13}$C NMR (126 MHz, DMSO-$d_6$) ϵ 172.06, 149.17, 139.16, 129.08, 109.65, 107.34, 105.00, 71.39, 71.21.

Example 7

$N^1,N^6$-Bis(3-aminophenyl)-D-glucaramide

In a dry box, MPD (0.67 g, 6.21 mmol) and GDL (0.27 g, 1.55 mmol) were weighed into an oven-dried, 20-mL scintillation vial. A metal spatula was used to grind the crystalline MPD and homogenize the reaction mixture. The vial was heated to 100° C. for 17 hours and then cooled to room temperature. The resulting glassy solid was broken up and extracted with methylene chloride to remove excess MPD. $^1$H NMR (500 MHz, DMSO-$d_6$) δ 9.36 (s, 1H), 9.11 (s, 1H), 7.041 (s, 1H), 7.037 (s, 1H), 6.95 (t, J=8.0 Hz, 1H), 6.94 (t, J=8.0 Hz, 1H), 6.78 (m, 2H), 6.30 (m, 2H), 4.23 (d, J=3.7 Hz, 1H), 4.11 (d, J=7.1 Hz, 1H), 4.05 (t, J=3.5 Hz, 1H), 3.84 (dd, J=3.7, 6.5 Hz, 1H). $^{13}$C NMR (126 MHz, DMSO-$d_6$) δ 171.33, 170.83, 148.93, 148.88, 139.23, 138.94, 128.90, 128.84, 109.62, 109.52, 107.52, 107.46, 105.19, 105.11, 73.75, 73.18, 72.53, 70.53.

Example 8

$N^1,N^6$-Bis(4-aminobenzyl)galactaramide

In a dry box, a solution of 4-aminobenzylamine (5.05 mL, 44.5 mmol) in DMSO (25 mL) was added to a slurry of DMG (5.05 g, 21.2 mmol) in DMSO (40 mL) in an oven-dried 200-mL round-bottom flask equipped with a magnetic stirbar. The resulting mixture was stirred at ambient temperature for five days and then filtered. The collected solid was washed with DMSO (10 mL) followed by methanol (75 mL) and then dried under vacuum to give a white solid (4.86 g). Water (400 mL) was added to the filtrate from the original reaction, and the mixture was stirred for 1 hour and then filtered. The recovered solid was washed with water (200 mL) followed by methanol (150 mL) and then dried under vacuum to give a second crop of white solid (2.93 g, 88% overall yield, 97+% purity). $^1$H NMR (DMSO-$d_6$) δ 7.72 (t, J=5.8 Hz, 2H), 6.94 (d, J=8.1 Hz, 4H), 6.49 (d, J=8.2 Hz, 4H), 5.19 (d, J=7.0 Hz, 2H), 4.89 (s, 4H), 4.38 (d, J=6 Hz, 2H), 4.16 (m, 6H), 3.82 (d, J=5.8 Hz, 2H). $^{13}$C NMR (DMSO-$d_6$) δ 173.0, 147.4, 128.2, 126.3, 113.7, 70.8, 70.7, 41.7.

Example 9

$N^1,N^6$-Bis(4-aminobenzyl)-D-glucaramide

In a dry box, 4-aminobenzylamine (7.33 mL, 64.7 mmol) was weighed into an oven-dried, 100-mL round-bottom flask equipped with a magnetic stirbar. Methanol (7 mL) and then a solution of GDL (5.00 g, 28.7 mmol) in methanol (10 mL) were added. Significant precipitation required addition of methanol (60 mL) to maintain stirring. The resulting slurry was stirred at ambient temperature for 24 hours and then filtered. The precipitate was washed with methanol (160 mL) and dried under vacuum to give a white solid (11.03 g, 92% crude yield). $^1$H and $^{13}$C NMR indicated that the product contained 4 mole % methyl N-(4-aminobenzyl)-D-glucaramate. Conversion was completed by reacting a portion of the crude product (10.38 g, 24.8 mmol) in 25 mL of DMSO with 4-aminobenzylamine (282 μL, 2.49 mmol) overnight at ambient temperature. The mixture was diluted with 75 mL of methanol and stirred several more hours. The resulting precipitate was isolated by filtration, washed with methanol (200 mL), and dried under vacuum to give a white solid (10.51 g, 100% yield). $^1$H NMR (500 MHz, DMSO-$d_6$) δ 8.04 (t, J=5.9 Hz, 1H), 7.77 (t, J=5.9 Hz, 1H), 6.94 (dd, J=2.5, 8.4 Hz, 4H), 6.50 (d, J=8.3 Hz, 4H), 5.53 (d, J=6.1 Hz, 1H), 5.37 (d, J=5.4 Hz, 1H), 4.91 (s, 4H), 4.76 (d, J=4.5 Hz, 1H), 4.62 (d, J=6.8 Hz, 1H), 4.15 (m, 4H), 4.07 (dd, J=2.7, 5.6, 1H), 3.99 (t, J=6 Hz, 1H), 3.96 (dt, J=6.5, 3 Hz, 1H), 3.77 (m, 1H). $^{13}$C NMR (126 MHz, DMSO-$d_6$) δ 173.01, 172.12, 147.60, 147.58, 128.44, 128.41, 126.45, 126.29, 113.88 (2C), 73.56, 73.23, 71.88, 70.60, 41.85, 41.79.

Example 10

$N^1,N^6$-Bis[(5-amino-1,3,3-trimethylcyclohexyl)methyl]galactaramide

DMG (1.00 g, 4.20 mmol) was heated at reflux for 2 hours in a solution of isophoronediamine (2.87 g, 16.9 mmol) in 20 mL of methanol. After the mixture had cooled and the solvent had been removed under reduced pressure, the resulting white solid was stirred for 1 hour in 100 mL of ether and filtered. The solid was washed further with three 20-mL portions of ether and then dried under vacuum to give 2.0 g (93% yield). LC-MS indicated that the product was a 7:1 mixture of the 2:1 and 3:2 adducts of isophoronediamine and DMG. The 2:1 adduct appeared as M+H$^+$, having an m/e of 515. The 3:2 adduct appeared as M+2H$^+$, having an m/e of 430. $^1$H NMR (500 MHz, DMSO-$d_6$) δ 7.32 (br s, 1H), 7.18 (br s, 1H), 4.16-4.09 (m, 2H), 3.78 (m, 2H), 2.86 (m, 4H), 3.95, 3.40 and 2.20 (3 m, 1H), 1.48 (m, 5H), 1.13-0.65 (m, 26H). $^{13}$C NMR (126 MHz, DMSO-$d_6$) δ 173.54, 172.54, 70.93 (4C), 52.38, 52.26, 49.75, 49.45, 47.22, 47.00, 44.98, 44.85, 43.77, 43.61, 36.44 (2C), 35.43 (2C), 31.72 (2C), 28.02, 27.81, 23.65 (2C).

Alternately, DMG (1.00 g, 4.20 mmol) and isophoronediamine (6.00 g, 35.2 mmol) were heated at 100° C. for 5 to 16 hours under a stream of nitrogen. The resulting glassy solid was triturated and washed with ether to give the product as a white granular solid.

Example 11

$N^1,N^6$-Bis[(5-amino-1,3,3-trimethylcyclohexyl)methyl]-D-glucaramide

GDL (2.00 g, 11.5 mmol) was added slowly to a solution of isophoronediamine (7.80 g, 45.8 mmol) in 25 mL of methanol. The mixture was stirred at room temperature for 1 hour and then at reflux for another hour. After the mixture had cooled and the solvent had been removed under reduced pressure, the resulting white solid was stirred for 1 hour in 100 mL of ether and filtered. The solid was washed further with three 25-mL portions of ether and then dried under vacuum to give 5.36 g (91% yield). LC-MS indicated that the product was a 77:20:3 mixture of the 2:1, 3:2, and 4:3 adducts of isophoronediamine and GDL. The 2:1 adduct appeared as M+H$^+$, having an m/e of 515. The 3:2 and 4:3 adducts appeared as M+2H$^+$, having an m/e of 430 and 602, respectively. Exact mass calculated for $C_{26}H_{50}N_4O_4$ (M+H$^+$) 515.3809, found 515.3801. $^1$H NMR (500 MHz, DMSO-$d_6$) δ 7.64-7.522 (m, 1H), 7.38-7.18 (m, 1H), 4.03 (br s, 1H), 3.98 (d, J=6.3 Hz, 1H), 3.88 (br s, 1H), 3.69 (m, 1H), 3.95, 3.52, 3.43 and 2.20 (4 m, 1H), 2.86 (m, 4H), 1.48 (m, 5H), 1.13-0.65 (m, 26H). $^{13}$C NMR (126 MHz, DMSO-$d_6$) δ 173.44, 172.46, 73.28 (2C), 71.74, 70.63, 52.38 (2C), 49.38 (2C), 47.08 (2C), 44.96 (2C), 43.56 (2C), 36.45 (2C), 35.34 (2C), 31.67 (2C), 27.97 (2C), 23.67 (2C).

Example 12

$N^1,N^4$-Bis[(5-amino-1,3,3-trimethylcyclohexyl)methyl]-L-tartaramide

Isophoronediamine (3.30 g, 19.4 mmol) and diethyl L-tartrate (1.00 g, 4.85 mmol) were combined in a 100-mL round-bottom flask and heated at 92° C. under a stream of nitrogen for 1 hour. The mixture was cooled, stirred for 1 hour in 100 mL of ether, and filtered. The solid collected was washed further with three 20-mL portions of ether and then dried under vacuum to give 1.88 g (85% yield). LC-MS indicated that the product was a 84:16 mixture of the 2:1 and 3:2 adducts of isophoronediamine and diethyl L-tartrate. The 2:1 adduct appeared as M+H$^+$, having an m/e of 455. The 3:2 adduct appeared as M+2H$^+$, having an m/e of 370. Exact mass calculated for $C_{24}H_{47}N_4O_4$ (M+H$^+$) 455.3597, found 455.3581. $^1$H NMR (500 MHz, DMSO-$d_6$) δ 7.39 (t, J=6.2 Hz, 1H), 7.33-7.25 (m, 1H), 4.26-4.16 (m, 2H), 3.96, 3.44 and 2.20 (3 m, 1H), 2.86 (m, 4H), 1.47 (m, 5H), 1.13-0.60 (m, 26H). $^{13}$C NMR (126 MHz, DMSO-$d_6$) δ 172.16 (2C), 72.84 (2C), 52.47, 52.42, 49.70, 49.64, 47.18, 47.02, 45.21, 45.11, 43.54 (2C), 36.41 (2C), 35.35 (2C), 31.69 (2C), 28.00, 27.97, 23.64, 23.60.

Dihydroxyaldaramides

Example 13

$N^1,N^6$-Bis(2-hydroxyethyl)-D-glucaramide

In a dry box, ethanolamine (0.72 mL, 11.8 mmol) was weighed into an oven-dried, 20-mL scintillation vial equipped with a magnetic stirbar. Methanol (1 mL) was added, and the solution was treated with a solution of GDL (1.00 g, 5.77 mmol) in methanol (3.5 mL). The resulting slurry was stirred at ambient temperature for 25 hours. The white solid formed was recovered by filtration, washed with methanol (18 mL), and dried under vacuum to give 1.02 g. The mother liquor was concentrated, and the resulting white solid was collected by filtration, washed with cold methanol (2 mL), and dried under vacuum to give an additional 0.21 g (73% overall yield). $^1$H NMR (DMSO-$d_6$) δ 7.75 (t, J=5.6 Hz, 1H), 7.54 (t, J=5.7 Hz, 1H), 5.55 (d, J=6.2 Hz, 1H), 5.38 (d, J=5.2 Hz, 1H), 4.73 (d, J=4.9 Hz, 1H), 4.65 (t, J=5.3 Hz, 2H), 4.57 (d, J=6.7 Hz, 1H), 3.99 (t, J=4.4 Hz, 1H), 3.94 (t, J=6.1 Hz, 1H), 3.87 (m, 1H), 3.71 (m, 1H), 3.41 (m, 4H), 3.16 (m, 4H). $^{13}$C NMR (DMSO-$d_6$) δ 173.2, 172.4, 73.2, 72.8, 71.7, 70.3, 59.8, 59.7, 41.1, 41.0.

Example 14

N$^1$,N$^6$-Bis(3-hydroxypropyl)-D-glucaramide

In a dry box, 3-amino-1-propanol (1.05 mL, 13.8 mmol) was weighed into an oven-dried, 20-mL scintillation vial equipped with a magnetic stirbar. Methanol (1 mL) was added, and the solution was treated with a solution of GDL (1.17 g, 6.71 mmol) in methanol (5 mL). The resulting slurry was stirred at ambient temperature for 24 hours. The white solid formed was recovered by filtration, washed with methanol (18 mL), and dried under vacuum to give 1.74 g (80% yield). $^1$H NMR (DMSO-$d_6$) δ 7.82 (t, J=5.7 Hz, 1H), 7.62 (t, J=5.8 Hz, 1H), 5.49 (d, J=6.0 Hz, 1H), 5.33 (d, J=4.9 Hz, 1H), 4.70 (d, J=4.6 Hz, 1H), 4.56 (d, J=6.6 Hz, 1H), 4.41 (t, J=5.1 Hz, 2H), 3.97 (t, J=3.8 Hz, 1H), 3.91 (t, J=6.0 Hz, 1H), 3.86 (m, 1H), 3.69 (m, 1H), 3.40 (dt, J=5.1, 6.5 Hz, 4H), 3.14 (dt, J=5.8, 6.5 Hz, 4H), 1.55 (quint, J=6.5 Hz, 2H), 1.54 (quint, J=6.5 Hz, 2H). $^{13}$C NMR (DMSO-$d_6$) δ 173.14, 172.28, 73.28, 72.94, 71.66, 70.38, 58.59 (2C), 35.78, 35.70, 32.17, 32.13.

Example 15

N$^1$,N$^6$-Bis[2-(4-hydroxyphenyl)ethyl]-D-glucaramide

To a solution of tyramine (0.54 g, 3.93 mmol) in methanol (10 mL) in a 20-mL scintillation vial equipped with a magnetic stirbar was added a solution of GDL (0.33 g, 1.88 mmol) in methanol (2 mL). The resulting solution was stirred at ambient temperature for 15 hours. The resulting white precipitate was collected by filtration, washed with methanol (15 mL), and dried under vacuum to give 0.62 g (74% yield). $^1$H (300 MHz, DMSO-$d_6$) δ 9.10 (br, 2H), 7.84 (br t, 1H), 7.58 (br t, 1H), 6.98 (d, J=7.8 Hz, 4H), 6.67 (d, J=7.8 Hz, 4H), 5.47 (br, 2H), 4.70 (br, 2H), 3.99 (s, 1H), 3.92 (m, 2H), 3.73 (br s, 1H), 3.24 (br s, 4H), 2.60 (br t, 4H). $^{13}$C NMR (75 MHz, DMSO-$d_6$) δ 173.28, 172.34, 155.83 (2C), 129.65 (6C), 115.37 (4C), 73.46, 73.11, 71.85, 70.61, 40.56, 40.46, 34.62, 34.54.

Bis(alkoxycarbonylalkyl)aldaramides

Example 16

N$^1$,N$^6$-Bis(methoxycarbonylmethyl)-D-glucaramide

In a dry box, glycine methyl ester hydrochloride (0.13 g, 1.05 mmol) was weighed into an oven-dried, 20-mL scintillation vial equipped with a magnetic stirbar. Methanol (4 mL) was added, and the solution was treated with triethylamine (0.22 mL, 1.58 mmol). After the resulting solution had stirred at ambient temperature for 10 minutes, a solution of GDL (0.92 g, 0.53 mmol) in methanol (2 mL) was added, and the resulting solution was stirred overnight at ambient temperature. The resulting white precipitate was collected by filtration, washed with methanol (4 mL), and dried under vacuum to give 88 mg (48% yield). $^1$H NMR (500 MHz, DMSO-$d_6$) δ 8.19 (t, J=5.8 Hz, 1H), 7.96 (t, J=5.8 Hz, 1H), 5.69 (d, J=5.8 Hz, 1H), 5.40 (d, J=4.5 Hz, 1H), 4.65 (d, J=4.2 Hz, 1H), 4.48 (d, J=6.0 Hz, 1H), 4.06 (br t, 1H), 4.01 (t, J=5.8 Hz, 1H), 3.95-3.76 (m, 6H), 3.622 (s, 3H), 3.618 (s, 3H). $^{13}$C NMR (126 MHz, DMSO-$d_6$) δ 173.82, 172.97, 170.46, 170.35, 73.25, 72.80, 71.930, 70.64, 51.90, 51.86, 40.68, 40.66.

Example 17

N$^1$,N$^6$-Bis[(1S)-1-(methoxycarbonyl)ethyl]-D-glucaramide

In a dry box, L-alanine methyl ester hydrochloride (1.145 g, 8.20 mmol) was dissolved in 10 mL of methanol in an oven-dried, 50-mL round-bottom flask equipped with a magnetic stirbar. Addition of solid sodium hydroxide (0.328 g, 8.20 mmol) and stirring at ambient temperature for thirty minutes resulted in a colorless slurry. A solution of GDL (0.714 g, 4.10 mmol) in methanol (10 mL) was added, and the mixture was stirred for two weeks at ambient temperature, forming a yellow-orange solution with precipitate. Evaporation of solvent under vacuum gave the product admixed with sodium chloride. $^1$H NMR (300 MHz, DMSO-$d_6$) δ 8.13 (d, J=7.3 Hz, 1H), 7.95 (d, J=7.2 Hz, 1H), 5.20 (br, 4H), 4.32 (quint, J=7 Hz, 1H), 4.30 (quint, J=7 Hz, 1H), 4.04 (d, J=3.5 Hz, 1H), 3.99 (d, J=5.6 Hz, 1H), 3.87 (t, J=2.9 Hz, 1H), 3.71 (dd, J=2.8, 5.3 Hz, 1H), 3.61 (s, 6H), 1.28 (d, J=7.2 Hz, 6H). $^{13}$C NMR (75 MHz, DMSO-$d_6$) δ 173.24, 173.02 (2C), 172.42, 73.26, 72.76, 71.71, 70.50, 52.16 (2C), 47.58, 47.52, 17.56, 17.35.

Example 18

N$^1$,N$^6$-Bis[(5S)-5-amino-5-(methoxycarbonyl)pentyl]-D-glucaramide

To a suspension of L-lysine methyl ester dihydrochloride (1.00 g, 4.29 mmol) in 10 mL of methanol was added 1.22 mL (8.16 mmol) of 1,8-diazabicyclo[5.4.0]undec-7-ene. A solution of GDL (373 mg, 2.14 mmol) in 2 mL of methanol was added dropwise to the resulting homogeneous solution. After the reaction had stirred at room temperature for 1 day, evaporation of solvent under vacuum and examination by $^1$H NMR showed the product to contain a 45:1 ratio of lysine acylated on the ε-amine versus the α-amine group. $^1$H NMR (500 MHz, DMSO-$d_6$) δ 7.82 (t, J=5.7 Hz, 1H), 7.59 (t, J=5.8 Hz, 1H), 3.97 (d, J=3.7 Hz, 1H), 3.91 (d, J=6.4 Hz, 1H), 3.85 (t, J=3.4 Hz, 1H), 3.66 (dd, J=2.9, 6.3 Hz, 1H), 3.59 (s, 6H), 3.27 (m, 2H), 3.04 (m, 4H), 1.53-1.26 (m, 12H). $^{13}$C NMR (126 MHz, DMSO-$d_6$) δ 176.27 (2C), 173.30, 172.33, 73.53, 73.19, 71.73, 70.57, 53.98 (2C), 51.56 (2C), 38.33, 38.25, 34.34 (2C), 29.05, 28.96, 22.68, 22.66.

Example 19

N$^1$,N$^6$-Bis[(5S)-5-amino-5-(methoxycarbonyl)pentyl]-D-glucaramide (Alternate Procedure)

To a solution of L-lysine methyl ester dihydrochloride (0.341 g, 1.46 mmol) in 5 mL of methanol was added a solution of sodium hydroxide (0.117 g, 2.93 mmol) in methanol (5 mL). After stirring at ambient temperature for 25 minutes, the mixture was filtered to remove insolubles, and a solution of GDL (0.127 g, 7.31 mmol) in methanol (5 mL) was added. The reaction stirred several days at ambient temperature, and solvent was removed under vacuum to give 0.296 g (75% yield). $^1$H NMR showed the product to contain a 17:1 ratio of lysine acylated on the ε-amine versus lysine acylated on the α-amine group.

Bis(carboxyalkyl)aldaramides

Example 20

$N^1,N^6$-Bis[(1S)-1-carboxyethyl]-D-glucaramide

In a dry box, solid sodium hydroxide (0.449 g, 11.2 mmol) was added to a slurry of L-alanine (1.00 g, 11.2 mmol) in methanol (10 mL) in an oven-dried, 50-mL round-bottom flask equipped with a magnetic stirbar. The mixture stirred at room temperature for three hours, resulting in a colorless solution. GDL (0.977 g, 5.61 mmol) in methanol (8 mL) was added, and the mixture was stirred for 18 hours at ambient temperature. Methanol (6 mL) was added to the clay-like reaction mixture to facilitate stirring for an additional 24 hours. Attempted recovery of the product by filtration failed due to clogging of the fritted glass funnel. Evaporation of the solvent under vacuum gave the product as its disodium salt (1.091 g, 49% yield): $^1$H NMR (300 MHz, D$_2$O) δ 4.31 (br s, 1H), 4.26 (d, J=5.4 Hz, 1H), 4.19 (q, J=7.1 Hz, 2H), 4.11 (br s, 1H), 3.95 (t, J=4.7 Hz, 1H), 1.37 (d, J=7.1 Hz, 6H). $^{13}$C NMR (75 MHz, D$_2$O) δ 180.14, 179.98, 173.59 (2C), 73.63, 73.33, 72.60, 71.07, 51.20, 51.14, 18.50, 18.24. Treatment of the disodium salt with stoichiometric HCl gave the dicarboxylic acid: $^1$H NMR (300 MHz, DMSO-d$_6$) δ 7.90 (d, J=6.9 Hz, 1H), 7.73 (d, J=6.8 Hz, 1H), 4.23 (q, J=6.6 Hz, 2H), 4.03 (br s, 1H), 3.98 (d, J=5.3 Hz, 1H), 3.89 (br s, 1 H), 3.72 (br s, 1H), 1.28 (d, J=6.7 Hz, 6H). $^{13}$C NMR (75 MHz, DMSO-d$_6$) δ 174.25, 174.21, 172.94, 172.11, 73.48, 72.77, 71.74, 70.49, 47.71, 47.65, 18.14, 17.85.

Example 21

$N^1,N^6$-Bis[(1S)-1-carboxybutyl]-D-glucaramide

Solid sodium hydroxide (0.125 g, 3.13 mmol) was added to a slurry of L-norvaline (0.366 g, 3.13 mmol) in methanol (11 mL) in an oven-dried, 50-mL round-bottom flask equipped with a magnetic stirbar. The mixture stirred at room temperature for 30 minutes, resulting in a colorless solution. GDL (0.272 g, 1.56 mmol) in methanol (6 mL) was added, and the mixture was stirred for 85 hours at ambient temperature. The resulting precipitate was collected by filtration, washed with methanol (8 mL), and dried under vacuum to give 0.186 g (25% yield). $^1$H NMR (D$_2$O) δ 4.31 (d, J=3.4 Hz, 1H), 4.29 (d, J=5.5 Hz, 1H), 4.22 (t, J=4.8 Hz, 2H), 4.21 (t, J=4.5 Hz, 4H), 4.12 (dd, J=3.6, 4.1 Hz, 1H), 3.97 (dd, J=4.4, 5.1 Hz, 1H), 1.77 (m, 4H), 1.32 (m, 4H), 0.89 (t, J=7.5 Hz, 6H). $^{13}$C NMR (D$_2$O) δ 179.7, 179.6, 173.8, 173.6, 73.3, 73.2, 72.7, 71.0, 55.3, 55.2, 34.4, 34.2, 19.0, 18.9, 13.5 (2C).

Example 22

$N^1,N^6$-Bis[(5S)-5-amino-5-carboxypentyl]-D-glucaramide

Saponification of $N^1,N^6$-bis[(5S)-5-amino-5-(methoxycarbonyl)pentyl]-D-glucaramide gave $N^1,N^6$-bis[(5S)-5-amino-5-carboxypentyl]-D-glucaramide as its double internal salt. $^1$H NMR (D$_2$O) δ 4.30 (d, J=3.2 Hz, 1H), 4.23 (d, J=5.6 Hz, 1H), 4.08 (dd, J=3.6, 4.6 Hz, 1H), 3.94 (dd, J=4.7, 5.6 Hz, 1H), 3.73 (t, J=6.0 Hz, 2H), 3.27 (t, J=7.2 Hz, 4H), 1.88 (m, 4H), 1.59 (m, 4H), 1.40 (m, 4H). $^{13}$C NMR (D$_2$O) δ 175.2 (2C), 174.5, 174.3, 73.4, 73.3, 72.8, 71.2, 55.2 (2C), 39.1 (2C), 30.5 (2C), 28.5 (2C), 22.2 (2C).

Example 23

$N^1,N^6$-Bis[(5S)-5-(tert-butoxycarbonylamino)-5-carboxypentyl]-D-glucaramide To a solution of $N^ε$-tert-butoxycarbonyl-L-lysine (2.094 g, 8.50 mmol) in 15 mL of methanol was added a solution of sodium hydroxide (340 mg, 8.50 mmol) in 15 mL of methanol, followed by a solution of GDL (740 mg, 4.25 mmol) in 15 mL of methanol. After the reaction had stirred at room temperature for 1 day, the solvent was evaporated under vacuum to give the product as its disodium salt. $^1$H NMR (300 MHz, methanol-d$_4$) δ 4.21 (d, J=2.9 Hz, 1H), 4.14 (d, J=6.4 Hz, 1H), 4.10 (t, J=2.8 Hz, 1H), 3.93 (m, 2H), 3.89 (dd, J=2.6, 6.4 Hz, 1H), 3.24 (t, J=6.5 Hz, 4H), 1.82-1.384 (m, 12H), 1.43 (s, 18H). $^{13}$C NMR (75 MHz, methanol-d$_4$) δ 179.80 (2C), 175.44, 174.94, 157.60 (2C), 79.96 (2C), 75.06, 75.00, 73.37, 71.72, 57.14 (2C), 39.83 (2C), 33.80 (2C), 30.08 (2C), 28.81 (6C), 23.78 (2C).

What is claimed:

1. A process for preparing a compound of Formula VII

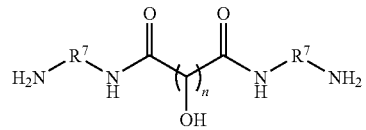

or salt thereof, comprising contacting at least one diamine of the formula NH2-R7-NH2 with a compound of Formula VIII, IX, or X

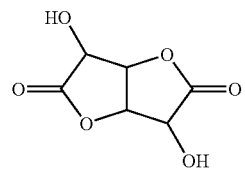

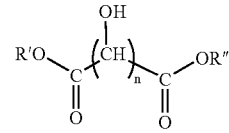

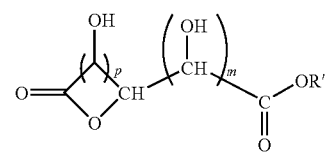

wherein R7 is an optionally substituted hydrocarbylene group, wherein the hydrocarbylene group is aliphatic or aromatic, linear, branched, or cyclic, the hydrocarbylene group optionally contains —O— linkages, R' and R" are independently selected from 1 to 6 carbon alkyl groups, n=1-6, m=0-4, and p=1-4.

2. The process of claim 1 wherein n=4.

3. The process of claim 1 wherein R7 is an alkylene, polyoxaalkylene, or arylene group, linear or branched, and wherein the alkylene, polyoxaalkylene, or arylene group is optionally substituted with NH2 or alkyl.

4. The process of claim 1 wherein the diamine is selected from:

H2NCH2CH2NH2, H2NCH2(CH2)4CH2NH2, and compounds of Formula XI, Formula XII, and Formula XIII

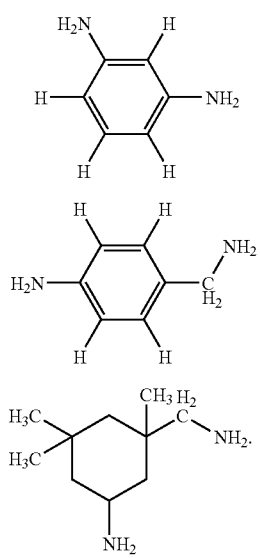

5. A process for preparing a compound of Formula XIX

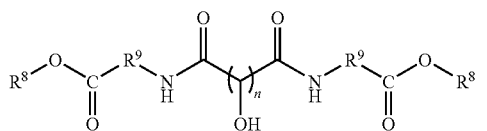

or a salt thereof, comprising contacting at least one amino acid or amino acid ester of the formula (R8OOC)—R9-NH2 with a compound of Formula VIII, IX, or X

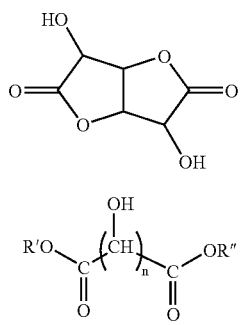

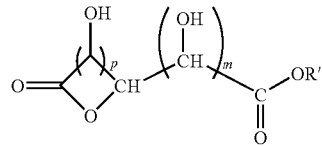

wherein n=1-6; R9 is an optionally substituted hydrocarbylene group, wherein the hydrocarbylene group is aliphatic or aromatic, linear, branched, or cyclic, and wherein the hydrocarbylene group optionally contains —O— linkages, R8 is hydrogen, optionally substituted aryl or optionally substituted alkyl, R' and R" are independently a 1 to 6 carbon alkyl group, n=1-6, m=0-4, and p=1-4.

6. The process of claim 5 wherein n=4.

7. The process of claim 5 wherein R9 is an alkylene, polyoxaalkylene, or arylene group, linear or branched, and wherein the alkylene, polyoxaalkylene, or arylene group is optionally substituted with NH2 or alkyl.

8. The process of claim 5 wherein the amino acid or amino acid ester is selected from: H2NCH2C(=O)OCH3, H2NCH(CH3)C(=O)OCH3, H2N(CH2)4CH(NH2)C(=O)OCH3, H2NCH(CH3)C(=O)OH, H2N(CH2)4CH(NH2)C(=O)OH, and compounds of Formula XX

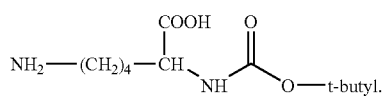

9. A process for preparing a compound of Formula XXII

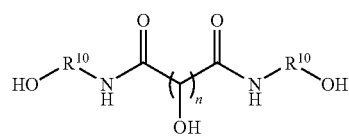

or salt thereof, comprising contacting at least one aminoalcohol of Formula HO—R10-NH2 with a compound of Formula VIII or X

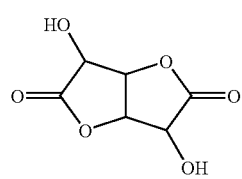

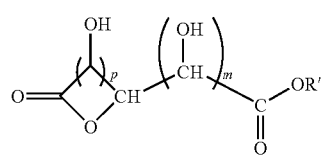

wherein R10 is an optionally substituted hydrocarbylene group, wherein the hydrocarbylene group is aliphatic or aromatic, linear, branched, or cyclic, and wherein the hydrocarbylene group optionally contains —O— linkages, R' is a 1 to 6 carbon alkyl group, m=0-4, and p=1-4.

10. The process of claim 9 wherein m is 1 and p is 2.

11. The process of claim 9 wherein R10 is an alkylene, polyoxaalkylene, or arylene group, linear or branched, and wherein the alkylene, polyoxaalkylene, or arylene group is optionally substituted with NH2 or alkyl.

12. The process of claim 9 wherein the aminoalcohol is HO—(CH2)2-NH2, HO—(CH2)3-NH2, or 4-(2-aminoethyl)-phenol.

13. The process of claim 1, 6, or 9 wherein the contacting is performed in a solution with one or more suitable solvents.

14. The process of claim 13 wherein the suitable solvent is water, dimethylformamide, dimethylformamide LiCl, dimethylacetamide, dimethylacetamide LiCl, ethanol or methanol.

15. The process of claim 1, 6, or 9 wherein the contact is performed in the absence of a solvent.

16. The process of claim 13 wherein the contact is performed at a temperature of 20 ° C. to 130 ° C.

* * * * *